United States Patent [19]

Zadra et al.

[11] 4,098,718

[45] Jul. 4, 1978

[54] SOAPS OF MALEIC ANHYDRIDE ADDUCTS OF ALPHA-METHYLSTYRENE AND ALPHA-METHYLSTYRENE DIMER

[75] Inventors: Mario D. Zadra, Barberton; James J. Tazuma, Stow, both of Ohio

[73] Assignee: The Goodyear Tire & Rubber Company, Akron, Ohio

[21] Appl. No.: 790,112

[22] Filed: Apr. 22, 1977

[51] Int. Cl.² ............................................. B01F 17/00
[52] U.S. Cl. ............................. 252/356; 260/23 EM; 260/23.7 A; 260/29.7 EM; 260/29.7 R; 526/213; 526/911
[58] Field of Search .................. 252/356; 526/15, 911

[56] References Cited

U.S. PATENT DOCUMENTS

| | | | |
|---|---|---|---|
| 2,283,214 | 5/1942 | Kyrides | 252/356 X |
| 2,561,313 | 7/1951 | Malinowski | 260/22 CB |
| 2,607,762 | 8/1952 | Bowen | 526/15 X |
| 2,712,003 | 6/1955 | Bowen | 526/15 X |
| 2,913,482 | 11/1959 | Dazzi | 260/28.5 R |

OTHER PUBLICATIONS

Encyclopedia of Science and Technology, vol. 1, Interscience Pub. Div. of John Wiley & Sons, Inc., 1964, pp. 76-84, 87, 88 and 93-95.

*Primary Examiner*—Richard D. Lovering
*Attorney, Agent, or Firm*—J. A. Rozmajzl; D. B. Little

[57] ABSTRACT

Stable surface-active agents are produced by neutralizing the reaction product of maleic anhydride adducts of alpha-methylstyrene compounds and alpha-methylstyrene dimer compounds with sodium and potassium hydroxide solution.

9 Claims, No Drawings

SOAPS OF MALEIC ANHYDRIDE ADDUCTS OF ALPHA-METHYLSTYRENE AND ALPHA-METHYLSTYRENE DIMER

BACKGROUND OF THE INVENTION

The present invention relates to the stabilization of aqueous dispersions. More particularly, it relates to surface active agents synthesized from maleic anhydride adducts of alpha-methylstyrene and alpha-methylstyrene dimer which are useful as stabilizers in rubber latex.

Various dimers of styrene and styrene derivatives are discussed in Griess, G. A., "Styrene Resins," in *Styrene, its Polymers, Copolymers and Derivatives*, Boundy, R. H. and Boyer, R. F., ed., Part II, pp. 812–814, Reinhold, N.Y., 1952 (hereinafter referred to as Griess).

The greater part of the work reported in the literature on reaction products of styrene and alpha-methylstyrene and maleic anhydride is on the subject of radical catalyzed polymerization. Relatively little effort has been devoted to investigating products other than copolymers.

Reactions between maleic anhydride and styrene and alpha-methylstyrene are the subject of several references. The addition of maleic anhydride to styrene is described in Patai, S. ed., *The Chemistry of Alkenes*, pp. 873–894, Interscience Pub., N.Y., 1964. An adduct of alpha-methylstyrene with maleic anhydride is mentioned in Onishchenko, A. S., *Diene Synthesis*, p. 494, Academy of Sciences of the USSR, Institute of Organic Chemistry, Daniel Davey Pub., N.Y., 1964. Other references to reactions between alpha-methylstyrene and maleic anhydride are: CA 37:5034 (1943); CA 45:9894 (1951); and U.S. Pat. No. 2,561,313.

An adduct between styrene and its homologs including alpha-methylstyrene dimer and fumarate esters is reported in U.S. Pat. No. 2,913,482.

SUMMARY OF THE INVENTION

The principal object of this invention is to provide a novel surface-active agent that will produce polymer emulsions of high stability.

It is a further object of this invention to provide a process for preparing the surface-active agents previously mentioned. Other objects and advantages will hereinafter appear.

The principal object is accomplished by neutralizing the adduct of maleic anhydride and either alpha-methylstyrene, its derivatives, or alpha-methylstyrene dimer or its derivatives, with sodium or potassium hydroxide solution. The derivatives of alpha-methylstyrene and alpha-methylstyrene dimer have structural formulae as follows:

Alpha-methylstyrene derivatives (I)

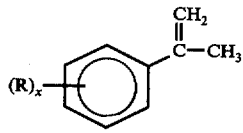

wherein R is selected from the group consisting of hydrogen, methyl, ethyl, isopropyl, t-butyl and isobutyl, and x is one or two.

Alpha-methylstyrene dimer derivatives (II)

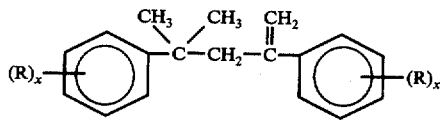

wherein R and x are the same as defined above.

Alpha-methylstyrene is commercially available and for that reason is preferred over the dimer as a raw material. The adduct of maleic anhydride and alpha-methylstyrene or its derivatives can be formed by reacting the two materials with or without a free radical catalyst (e.g. an organic peroxide) and with or without the presence of solvent. Although any molar ratio of maleic anhydride to alpha-methylstyrene can be utilized, a ratio of 1.5:1 to 3:1 is preferred for reasons of economy. These ratios help to insure the complete utilization of the alpha-methylstyrene. Reaction temperature has ranged from 45° to 210° C. Both reactants may contain inhibitor such as 4-t-butylcatechol in small concentrations of approximately one weight percent or less. Batch reaction time has varied from 0.2 to 6.0 hours.

The order of addition of the reactants can also be varied. The alpha-methylstyrene may be slowly added to maleic anhydride at the reaction temperature. Maleic anhydride may be slowly added to the alpha-methylstyrene, or they may both be premixed together in the reactor. The reactant addition time in experimental work has ranged between 0.1 and 0.6 hours.

The reaction described may result in a considerable amount of polymeric material (copolymer of alpha-methylstyrene and maleic anhydride with a molecular weight greater than 1500). Indeed, the reaction conditions affect the relative production of addition product and copolymer. Copolymer is most favored when: the maleic anhydride to alpha-methylstyrene mole ratio is one or less, temperature is below 150° C., and/or the reaction is carried out in the presence of a peroxide catalyst. Addition products (oligomers) formation predominates when: maleic anhydride to alpha-methylstyrene mole ratio is higher than one, temperature is above 150° C., and free-radical catalyst is absent. Above 200° C., the formation of copolymer is virtually completely inhibited. It is preferred that production of copolymer be minimized.

Solvents which have been used are ortho-dichlorobenzene and benzene, but is preferred that no solvent be used.

For purposes of this invention, the term "adduct" does not mean a pure addition product. Rather, it means a mixture of oligomers of the two principal reactants (and copolymer in the case of alpha-methylstyrene). A pure, single component product is not critical to this invention. The reactions herein described produce a mixture which is neutralized to the desired product.

The individual components of the reaction products are difficult to separate and identify with certainty. In the case of the alpha-methylstyrene and its derivatives, it is believed that Diels-Alder and olefin addition reactions occur resulting in a mixture of oligomers having one, two or three maleic anhydride units per alpha-methylstyrene unit. The principal product (beside copolymer) is believed to be Cotetramer (III)

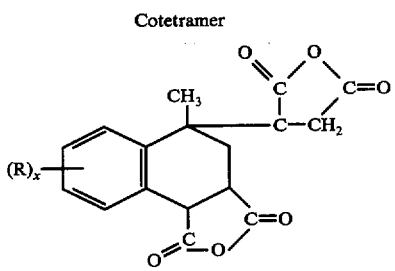

Unreacted material may be removed from the reactor by vacuum distillation.

The adduct is characterized by a softening point (as measured by ASTM Method No. E28-67) between 100 and 180 and by an acid number between 520 and 750.

The adduct of maleic anhydride and alpha-methylstyrene dimer is also a mixture of oligomers, but without any appreciable amount of copolymer.

The three forms of alpha-methylstyrene dimer identified are 2,4-diphenyl-4-methyl-1-pentene, 2,4-diphenyl-4-methyl-2-pentene, and 1,1,3-trimethylphenylindane. For purposes of adduct formation, 2,4-diphenyl-4-methyl-1-pentene is preferred. The 1,1,3-trimethylphenylindane is not reactive, and the 2,4-diphenyl-4-methyl-2-pentene is much less reactive than the preferred dimer. Therefore, in any mixture of dimers, it is preferred that the predominant specie be 2,4-diphenyl-4-methyl-1-pentene, or one of the derivatives (II) discussed previously.

It is thus a mixture of dimers to which the term "alpha-methylstyrene dimer" refers. That mixture preferably contains only a minimal amount of alpha-methylstyrene trimer. Although trimer does react with maleic anhydride, the conversion is incomplete (approximately 40% in 6 hours). The trimer remaining causes a separation problem after neutralization if present in substantial amounts (20 to 30 weight percent). It forms an oil which settles out of the soap. Trimer can be removed from the mixture by distillation before the reaction with maleic anhydride.

A process for producing alpha-methylstyrene dimer with a high selectivity for 2,4-diphenyl-4-methyl-1-pentene is described in Belgian Pat. No. 821,943.

The adduct of alpha-methylstyrene dimer with maleic anhydride may be formed by thermal reaction with or without catalyst (e.g. organic peroxide) in a manner similar to that previously described for alpha-methylstyrene. The dimer is slower to react than the alpha-methylstyrene and for that reason is somewhat less preferred.

In experiments, the following parameters were studied: mole ratio of maleic anhydride to dimer varied from 0.5 to 3., reaction temperature varied from 100° to 195° C., and reaction time varied from 1 to 6 hours. As the charge ratio was increased, the amount of maleic anhydride reacting increased and the products shifted to the higher anhydrides.

From an economic standpoint there is an advantage to completely reacting the alpha-methylstyrene dimer. It is an expensive raw material which should be totally utilized. To avoid leaving unreacted dimer at the end of the reaction it is preferred that 2 to 3 moles of maleic anhydride be charged per mole of alpha-methylstyrene dimer. Also, the di- and tri-anhydrides are preferred because they are believed to be effective.

For the same economic reason, it is felt that high reaction temperatures, in the range of 150° to 210° C. are preferred. In experiments, it was found that lower temperatures favored formation of dianhydride, and above 140° C. products with molecular weights greater than 432 (corresponding to tri- and tetra-anhydrides) were formed at the expense of the dianhydride.

An increase in the reaction time generally causes an increase in uptake of maleic anhydride.

The color of the adduct is affected by the order of addition of the reactants, reaction time, and temperature. Color numbers of 3 to 17 on the Gardner Scale have been obtained. A low color number was obtained when maleic anhydride was added to the dimer. Darker resins resulted when: the order of addition was reversed, reaction time was increased, and temperature was increased.

The adduct resin product is stripped at reduced pressures and 140° to 195° C. to remove unreacted dimer and maleic anhydride.

Again, the resulting product is a mixture of oligomers. It is believed that Diels-Alder and olefin addition reactions occur resulting in a mixture of oligomers having one, two, three, or four maleic anhydride units per alpha-methylstyrene dimer unit. The mono- and di-anhydride oligomers are believed to have the following structures:

mono-anhydride (IV)

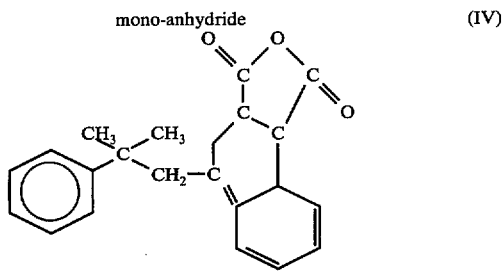

di-anhydride (V)

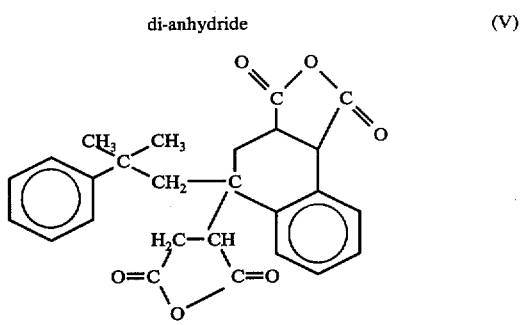

The adduct is characterized by: molecular weight ranging from 334 to 628, acid number of approximately 582, and softening point (ASTM E-28-67) of approximately 130.

Neutralization, for purposes of this invention, is defined as treating the adduct (maleic anhydride with either alpha-methylstyrene, alpha-methylstyrene dimer, or one of their derivatives as defined previously) with water and an alkali metal hydroxide, such as sodium hydroxide or potassium hydroxide. The anhydride units in the adduct are hydrolyzed to carboxylic acid groups by the water, and these groups are neutralized by the alkali metal hydroxide to form the alkali metal salt of the adduct.

Sufficient water is used to keep the adduct salt in solution. A convenient range of concentrations is from 10 to 30 weight percent adduct salt in water.

The amount of alkali metal salt is determined by the acid number of the adduct just before neutralization. Acid number is defined as milligrams of potassium hydroxide required to neutralize one gram of the sample, and that is the minimum weight of potassium hydroxide per gram of adduct which is utilized in the practice of this invention. In the case of another alkali metal hydroxide, the gram equivalent of the potassium hydroxide previously determined is utilized. Generally, the pH of the final product solution varies from 9 to 12.

DESCRIPTION OF THE PREFERRED EMBODIMENTS

This invention will be better understood from a consideration of the following examples given for the sake of illustration, but with no intention of limiting the scope of the invention. Percentages stated are by weight.

EXAMPLE I

Alpha-Methylstyrene Maleic Anhydride Adduct and Soap Preparation

Maleic anhydride (100 grams) was added to a three-necked 250cc flask equipped with a stirrer, condenser, thermometer and addition funnel and heated to 150° C. To this was added 80.2 grams of alpha-methylstyrene over a period of 30 minutes, allowing the exotherm to raise the temperature to 165° to 170° C. This reaction mixture was stirred an additional one hour then stripped of volatiles at a pot temperature of 180° C. and 0.5 mm Hg pressure for one hour. A clear, light amber product was recovered having a softening point of 144.5° C. and an acid number of 645. It contained 22 weight percent copolymer of alpha-methylstyrene and maleic anhydride.

To a 2-liter resin pot equipped with stirrer, condenser, and thermometer was added 150 grams of the above adduct (including the copolymer), 96.8 g. KOH, and 1187 grams water and the mixture was heated to 90° to 95° C. After 5 to 6 hours most of the solids dissolved. The resultant mixture was cloudy and tan and had a pH of 10 and solid content of 17.7 percent.

EXAMPLE II

Alpha-Methylstyrene Dimer Maleic Anhydride Adduct and Soap Preparation

Maleic anhydride (249.4 grams) and alpha-methylstyrene dimer (200 grams) were reacted at 160° C. as previously described for alpha-methylstyrene over a period of 4 hours. An opaque, light amber product was obtained having a softening point of 130° C. and an acid number of 580.

The soap was similarly prepared by reacting 290 grams of the adduct II with 161 grams KOH (95% of requirement), and 1353 grams of water. After 7 to 8 hours at 90° to 95° C. most of the solids dissolved. This solution was cloudy and light amber and had a pH of 11. The solid content was 26.6 percent.

The alpha-methylstyrene dimer utilized in Example II had the following composition:
1,1,3-trimethyl-3-phenylindane — 10.9%
2,4-diphenyl-4-methyl-1-pentene — 68.6%
2,4-diphenyl-4-methyl-2-pentene — 20.5%

Surface-active agents herein described have been useful in emulsion polymerization systems as a stabilizer. Stabilizers are added to the soap solution in emulsion reaction systems in order to control flocculation or gum formation. They are used at levels ranging from 0.4 to 1.0 parts by weight per 100 parts by weight of monomer.

The process of using the surface-active agents of this invention is described in detail in a patent application Ser. No. 790,113 by Paul H. Sandstrom, entitled: "Process for Stabilizing Latex and Stable Latices Produced Thereby" filed the same day as this application Apr. 22, 1977.

While certain representative embodiments and details have been shown for the purpose of illustrating the invention, it will be apparent to those skilled in this art that various changes and modifications may be made therein without departing from the spirit or scope of the invention.

What is claimed is:

1. An organic oligomer surface-active agent made by the process steps comprising:
    (a) reacting a styrene derivative selected from the group consisting of (1) alpha-methylstyrene derivatives having the following molecular structure:

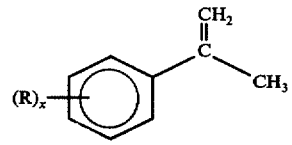

wherein R is selected from the group consisting of hydrogen, methyl, ethyl, isopropyl, t-butyl, and isobutyl, and x is 1, or 2; and (2) alpha-methylstyrene dimer derivatives having the following molecular structure:

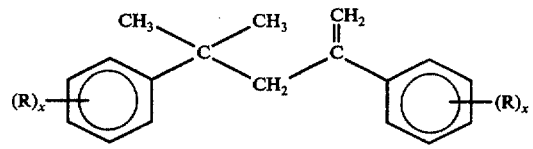

with maleic anhydride, wherein the reaction is carried out:
    (1) in the absence of a free radical catalyst;
    (2) at a molar ratio of maleic anhydride to styrene derivative of 1.5 to 3 in the case of alpha-methylstyrene derivatives and 0.5 to 3 in the case of alpha-methylstyrene dimer derivatives; and
    (3) at a temperature from 150° to 210° C. in the case of alpha-methylstyrene derivatives and 100° to 210° C. in the case of alpha-methylstyrene dimer derivatives; and
    (b) neutralizing the oligomer reduction product in (a) by treating it with water and an alkali metal hydroxide.

2. The surface-active agent of claim 1 which is in an aqueous solution comprised of from 10 to 30 weight percent surface-active agent and from 70 to 90 weight percent water which solution has a pH of from 9 to 12.

3. The surface active agent of claim 2 wherein the styrene derivative of step (a) is selected from the group consisting of alpha-methylstyrene and alpha-methylstyrene dimer.

4. The surface active agent of claim 3 wherein the alkali metal hydroxide is selected from the group consisting of sodium hydroxide and potassium hydroxide.

5. The surface-active agent of claim 4 wherein the process further comprises the step of removing unreacted material from the product of step (a) before step (b).

6. The surface-active agent of claim 5 wherein the unreacted material from step (a) is removed by vacuum distillation.

7. The surface-active agent of claim 5 made by the process wherein the styrene derivative is alpha-methylstyrene.

8. The surface-active agent of claim 5 made by the process wherein the styrene derivative is alpha-methylstyrene dimer.

9. The surface-active agent of claim 8 made by the process wherein step (a) is carried out with a ratio of 2 to 3 moles of maleic anhydride per mole of alpha-methylstyrene dimer, the order of reactant addition in step (a) is to add the maleic anhydride to the alpha-methylstyrene dimer, and wherein the reaction temperature in step (a) is between 150° and 210° C.

* * * * *

UNITED STATES PATENT AND TRADEMARK OFFICE
CERTIFICATE OF CORRECTION

PATENT NO. : 4,098,718
DATED : July 4, 1978
INVENTOR(S) : Mario D. Zadra et al

It is certified that error appears in the above-identified patent and that said Letters Patent are hereby corrected as shown below:

In Column 1, Line 28, "873" should be --893--.

Signed and Sealed this

Thirtieth Day of January 1979

[SEAL]

Attest:

RUTH C. MASON
Attesting Officer

DONALD W. BANNER
Commissioner of Patents and Trademarks